(12) United States Patent
Darbha et al.

(10) Patent No.: US 9,650,354 B2
(45) Date of Patent: May 16, 2017

(54) PROCESS FOR PRODUCING FURAN AND ITS DERIVATIVES

(71) Applicant: Council of Scientific & Industrial Research, New Delhi (IN)

(72) Inventors: Srinivas Darbha, Maharashtra (IN); Bhogeswararao Seemala, Maharashtra (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 0 days.

(21) Appl. No.: 14/392,288

(22) PCT Filed: Jun. 25, 2014

(86) PCT No.: PCT/IN2014/000422
§ 371 (c)(1),
(2) Date: Dec. 23, 2015

(87) PCT Pub. No.: WO2014/207764
PCT Pub. Date: Dec. 31, 2014

(65) Prior Publication Data
US 2016/0297787 A1  Oct. 13, 2016

(30) Foreign Application Priority Data
Jun. 25, 2013 (IN) .......................... 1869/DEL/2013

(51) Int. Cl.
*C07D 307/34* (2006.01)
*C07D 307/36* (2006.01)
*B01J 21/04* (2006.01)
*B01J 23/44* (2006.01)

(52) U.S. Cl.
CPC ............ *C07D 307/36* (2013.01); *B01J 21/04* (2013.01); *B01J 23/44* (2013.01)

(58) Field of Classification Search
CPC .................................................... C07D 307/34
USPC ........................................................ 549/429
See application file for complete search history.

(56) References Cited

U.S. PATENT DOCUMENTS 8,404,871 B2    3/2013  Li
2010/0099895 A1  4/2010  Wabnitz et al.

OTHER PUBLICATIONS

Wang et al., Energy & Environmetal Science, vol. 5, No. 8, 2012, pp. 8244-8260.*
Xingyu Wang et al., Exploiting H-transfer reactions with RANEY Ni for upgrade of phenolic and aromatic biorefinery feeds under unusual, low-severity conditions, Energy & Environmental Science, May 17, 2012, pp. 8244-8260, vol. 5 No. 8.
International Search Report, mailed Oct. 14, 2014 in connection with PCT International Application No. PCT/IN2014/000422, filed Jun. 25, 2014.
Notification Concerning Transmittal of Copy of International Preliminary Report on Patentability (Chapter 1 of the Patent Cooperation Treaty), including an International Preliminary Report on Patentability and Written Opinion of the International Searching Authority, mailed Jan. 7, 2016 by the International Bureau of WIPO in connection with PCT International Application No. PCT/IN2014/000422, filed Jun. 25, 2014.

* cited by examiner

*Primary Examiner* — Niloofar Rahmani
(74) *Attorney, Agent, or Firm* — John P. White; Cooper & Dunham LLP

(57) ABSTRACT

An efficient, hydrogen gas-free, high yielding, moderate temperature and safe-to-handle process for producing furan and its derivatives from furfural, which comprises contacting furfural and water-isopropanol mixture with a supported Pd or Pt catalyst at a temperature in the range of 200-250° C., is reported.

11 Claims, No Drawings

PROCESS FOR PRODUCING FURAN AND ITS DERIVATIVES

CROSS-REFERENCE TO RELATED APPLICATIONS

This application is a §371 national stage of PCT International Application No. PCT/IN2014/000422, filed Jun. 25, 2014, claiming the priority of Indian Patent Application No. 1869/DEL/2013, filed Jun. 25, 2013, the contents of each of which are hereby incorporated by reference in their entirety.

The following specification particularly describes the invention and the manner in which it is to be performed.

FIELD OF THE INVENTION

The present invention relates to an improved, efficient hydrogen gas-free, safe-to-handle process for producing furan and its derivatives from furfural in high yield and selectivity.

BACKGROUND AND PRIOR ART OF THE INVENTION

Furan is a platform chemical used in the synthesis of specialty chemicals. It is also known as a fuel additive.

Conventionally, furan is synthesized by vapor-phase decarbonylation of furfural in the presence of steam and Zn—Fe or Zn—Mn chromite catalyst at 400° C. with steam to furfural molar ratio of 1:5 to 1:10 and gas hourly space velocity (GHSV) of 500-1000 h$^{-1}$. Furan yield of 85 to 90% on furfural was claimed (U.S. Pat. No. 2,374,149 and U.S. Pat. No. 2,776,981). Hydrogen and carbon dioxide are produced as by-products. High temperature operation in the conventional process results in breakdown of furan into heavy products, resulting in short-term deactivation of the catalysts. Further, when the process is operated at high temperatures, there is a corresponding requirement of heat energy and accordingly, the exit product vapors require a greater amount of cooling. In other words, the process becomes expensive.

According to U.S. Pat. No. 4,764,627, furan and derivatives can be produced by passing-vapors of furfural over a zeolite catalyst at a temperature (350-550° C.) and for a residence time effective to decarbonylate furfural. Furfural vapors are diluted with a carrier gas which is selected from the group consisting of hydrogen, carbon monoxide, carbon dioxide, methane, helium, argon, nitrogen and steam. Selectivity of furan, was low due to formation other products.

U.S. Pat. No. 4,780,552 teaches a process for preparation of furan by decarbonylation of furfural in the gas phase at elevated temperatures (250-400° C.), at a pressure of from 0.1 to 10 bar in the presence of hydrogen and a catalyst containing Pt, Rh or mixtures thereof and alkali metal (cesium). Furfural conversion of 90% and furan selectivity of 91-95% was obtained. But drop in conversion after 500 h of catalyst use is the drawback of this process.

According to U.S. Pat. No. 3,257,417 and U.S. Pat. No. 3,223,714, furfural is decomposed into furan and carbon monoxide on supported Pd surface at 200° C. This reaction is done in presence of an alkali metal carbonate or alkali metal acetate promoter. U.S. Pat. No. 8,404,871, US 2011/0201832 and US 2012/0157698 disclose the reaction of furfural on Pd over Al$_2$O$_3$ in presence of co-fed water and hydrogen at about 300° C. and with furfural to hydrogen molar ratio of 1:1 and weight hourly space velocity (WHSV) of furfural of 230 h$^{-1}$ giving rise to furan with a yield of 95%. Hydrogen is co-fed to help volatilize furfural and to extend the catalyst life. The co-feed water enhances the conversion of furfural from 90 to nearly 100%.

2-Methyl furan is produced by hydrodeoxygenation/ C═O hydrogenolysis of furfural. It has all the characteristics to be used a fuel additive. Methyl furan is produced through external supply of hydrogen which makes the process expensive.

U.S. Pat. No. 8,710,251 discloses synthesis of furan and related compounds by vapor-phase decarbonylation of furfural and derivatives using a palladium/metal aluminate catalyst. The process is effected by contacting furfural in vapor phase and hydrogen gas as co-feed at a temperature in the range of from about 270° C. to about 330° C. at ambient pressure.

Due to the industrial importance of furan and the drawbacks of prior-art processes including requirement of expensive hydrogen co-feed, need of alkali metal promoters and high temperature operation, a safe-to-handle and commercially economic process, green process is desirable.

The present invention overcomes the above-said drawbacks of the prior-art processes and discloses an improved process for producing furan and its derivatives from furfural at moderate temperatures and without using hydrogen-gas in the feed stream.

While the raw material furfural is conventionally obtained from petroleum feedstock, it can also be derived from the pentosan sugars of lignocellulosic biomass by methods known in the art (ChemSusChem, Year 2012, Vol. 5, pp. 751-761 and Sugar Technology, Year 2011, Vol. 13, issue 2, pp. 166-169). Use of biomass derived furfural leads to a sustainable process for production of furan.

OBJECTIVE OF THE PRESENT INVENTION

The main object of the present invention is to provide an improved, hydrogen-free, high yielding, safe-to-handle process, that operates at moderate temperature to produce compound of formula I from furfural in high yield

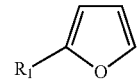

Formula I wherein R1 is selected independently from hydrogen or CH$_3$.

Yet another object of the invention is to provide an alkali metal free process for producing furan and methyl furan from furfural.

Still another object is to provide a hydrogen-free catalytic process for production of furan from furfural wherein the catalyst shows stable catalytic activity even after several recycles.

SUMMARY OF THE INVENTION

Accordingly, the present invention provides an improved process for the preparation of compound of formula I from furfural wherein improvement consist of adding water-isoproponal mixture into the furfural which leads to high conversion of furfural and high yield,

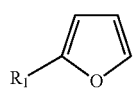

Formula I wherein R1 is selected independently from hydrogen or CH$_3$ the said process comprising contacting furfural and water-isopropanol mixture with a supported metal catalyst taken in the reactor in the presence of an inert gas as co-feed at a temperature in the range of 200-250° C. at inert gas pressure in the range 1 to 10 bar to obtain compound of formula I.

In an embodiment of the present invention furfural to water-isopropanol weight ratio ranges between 1:5 to 1:25.

In one embodiment of the present invention ratio of catalyst to furfural ranges between 2 and 5 wt %.

In another embodiment of the present invention supported metal catalyst used is selected from the group consisting of supported Pd or Pt catalyst and Pd or Pt content on the support ranges from 2-10 wt %

In another embodiment of the present invention support in supported metal catalyst is selected from the group consisting of alumina, ceria, zirconia, ceria-zirconia, sulphated zirconia, silica, carbon, clay, hydrotalcite, MgO—Al$_2$O$_3$ or mixtures thereof.

Still in another embodiment of the present invention the reaction is carried out in a semi-batch, continuous stirred tank or fixed-bed reactor.

Still in another embodiment of the present invention the inert gas is nitrogen, argon, helium or their mixtures.

Still in another embodiment of the present invention the water-iso-propanol mixture is in weight ratio ranging between 1:1 and 1:5.

Still in another embodiment of the present invention the catalyst is recyclable.

Still in another embodiment of the present invention conversion of furfural is in the range of 29-99.7 wt %.

Still in another embodiment of the present invention yield of compound of formula 1 is in the range of 68 90 wt %.

Still in another embodiment of the present invention furfural used in the process is obtained either from the conventional sources or from the pentosan sugars of ligno-cellulosic biomass by the methods known in the art (Chem-SusChem, Year 2012, Vol. 5, pp. 751-761 and Sugar Technology, Year 2011, Vol. 13, issue 2, pp. 166-169).

Still in another embodiment of the present invention the biomass-derived furfural is used without any pre-treatment or after purification.

In yet another embodiment of the present invention the reaction is carried out without using hydrogen gas.

DETAILED DESCRIPTION OF THE INVENTION

The present invention provides an improved process for preparation of furan and its derivatives from furfural. The present invention provides improved, hydrogen gas-free, high yielding, moderate temperature and safe-to-handle, green process for producing furan and its derivatives from furfural comprising contacting furfural and water-iso-propanol mixture with a supported Pd or Pt catalyst in the presence of an inert gas co-feed.

Furfural used in this process is obtained either from the conventional sources or from the pentosan sugars of ligno-cellulosic biomass by the methods known in art (Chem-SusChem, Year 2012, Vol. 5, pp. 751-761 and Sugar Technology, Year 2011, Vol. 13, issue 2, pp. 166-169).

Moreover, the hydrogen-free, moderate temperature, high yielding, safe-to-handle process of the present invention leads to production of furan and its derivative at the site of its raw material production itself and thereby, enabling value addition to biomass and employment/economic opportunities to rural sector.

The method of the present invention uses a supported Pd or Pt catalyst. It is a surprising discovery that the supported Pd or Pt catalyst of the present invention exhibits high activity and furan selectivity even without the use of hydrogen in the process. No side reactions are observed. More particularly, the catalyst is reusable. In the experiments leading to the present invention, it was found that the catalyst-supported Pd or Pt of the present invention is highly active yielding furfural conversion of 100 mol % and furan selectivity in the range of 75-90 mol %. Facile adsorption of furfural on active metal sites is the key factor responsible for the high catalytic activity of the catalyst of the present invention. While iso-propanol improves the stability, water enhances the activity and selectivity of the catalyst. Combination of both these solvents i.e., water and iso-propanol is essential for high activity and long time catalyst stability. Appropriate ratio of water and iso-propanol is critical for getting high conversion and furan yields. As this process is operated at moderate conditions, no waste streams are generated. Hence, the process of the present invention is safe and commercially easily adoptable.

The present invention discloses safe, efficient, hydrogen-free catalytic process for preparation of compound of formula I from furfural in high yield

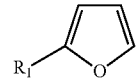

Formula I wherein R1 is selected independently from hydrogen or CH$_3$;

which comprises the steps of:
a) contacting furfural and water-isopropanol mixture with a supported Pd or Pt catalyst taken in the reactor in the presence of an inert gas as co-feed at a temperature in the range of 200-250° C., wherein furfural to water-isopropanol mixture weight ratio is in the range 1:5 and 1:25, inert gas is at a pressure in the range 1-10 bar, ratio of catalyst to furfural ranges between 2 and 5 wt %, and Pd or Pt content on the support ranges from 2-10 wt %, and
b) conducting the reaction at said temperature and pressure conditions, venting out the inert gas for recycle and separating the liquid product from catalyst by filtration followed by, distillation to obtain compound of formula (I).

The water to isopropanol mixture is in the ratio ranging between 1:1 to 1:5.

The catalyst of the present invention is Pd or Pt impregnated on a support selected from the group of alumina, ceria, zirconia, ceria-zirconia, sulphated zirconia, silica, carbon, clay, hydrotalcite, MgO—Al$_2$O$_3$ or the compositions containing these oxides and their mixtures.

In a feature of the present invention, the reaction is carried out either in a semi-batch or continuous batch/fixed-bed operation.

In another feature of the present invention, the process is carried out in the absence of alkali metal.

In yet another feature of the present invention, the inert gas is nitrogen, argon, helium or their mixture.

It is a feature of the present invention that the conversion of furfural is 100 mol % and furan selectivity is between 75 and 90 mol %.

It is another feature of the present invention that the catalyst in recyclable and reusable.

It is still another feature of the present invention that no waste streams are generated.

The supported Pd or Pt catalyst is prepared by wet impregnation method known in the art (Catalysis Letters, Year 2010, Vol. 140, pp. 55-64 and Journal of Catalysis, Year 2012, Vol. 285, pp. 31-40).

EXAMPLES

Following are the examples given to further illustrate the invention and should not be construed to limit the scope of the present invention.

Example 1

This example illustrates the preparation of the catalyst: 5 wt % Pd supported on alumina. To 1.484 g of 10 wt % aqueous tetraammine palladium (II) nitrate solution, 10 ml of distilled water was added. It was then added to 1 g of γ-$Al_2O_3$ taken in a glass round bottom flask. The suspension was mixed thoroughly and dried at 80° C. using a rotary evaporator. The solid obtained was recovered and dried at 100° C. for 6 h in an oven. Then, the material was calcined at 400° C. for 2 h. Prior to the reaction, catalyst was reduced under a flow of hydrogen (30 ml/min) at 250° C. for 2 h. Without exposing to atmosphere the catalyst was used in the reaction.

2 and 10 wt % $Al_2O_3$-supported Pd catalysts were prepared in the same manner taking 0.5749 g (for 2 wt % Pd/$Al_2O_3$) and 2.817 g (for 10 wt % Pd/$Al_2O_3$) of 10 wt % aqueous tetraammine palladium(II) nitrate solution, respectively.

Example 2

This example illustrates the preparation of 5 wt % Pt supported on alumina. 0.1052 g of tetraammine platinum(II) nitrate was dissolved in 10 ml of distilled water. This was then added to 1 g of γ-$Al_2O_3$ taken in a glass round bottom flask. It was mixed thoroughly and dried at 80° C. using a rotary evaporator. The solid obtained was recovered and dried at 100° C. for 6 h in an electric oven. Then, the material was calcined at 400° C. for 2 h. Prior to the reaction, catalyst was reduced under a flow of hydrogen (30 ml/min) at 350° C. for 2.5 h. Without exposing to atmosphere the catalyst was used in the reaction.

2 and 10 wt % $Al_2O_3$-supported Pt catalysts were prepared in the same manner taking 0.0816, and 0.222 g of tetraamineplatinum(II) nitrate, respectively.

The other supported Pt catalysts were prepared in the same manner taking appropriate support oxides and Pt precursor. Prior to deposition of the Pt, the commercial sulphated-$ZrO_2$, MgO and $SiO_2$ were activated at 120° C. for 2 h while γ-$Al_2O_3$ was activated at 150° C.

Example 3

This example illustrates the conversion of furfural to furan over Pd(5 wt %)/$Al_2O_3$ catalyst. 1 g of furfural (Aldrich Co.), 20 g of water were taken in a 100 ml stainless-steel reactor (Parr 4875 power controller and 4871 process controller). To that 0.05 g of the reduced Pd(5 wt %)/$Al_2O_3$ catalyst was added. The reactor was pressurized with nitrogen gas (5 bar). Temperature of the reactor was raised to 240° C. and the reaction was conducted for 2 h. Then the reactor was cooled to 25° C., gas was vented out for recycle purpose and the liquid product was separated from the catalyst by filtration. It was then subjected to analysis by gas chromatography (GC; Varian 3400; CP-SIL5CB column; 60 m-long and 0.25 mm-i.d.). The products were identified by GC-MS (Shimadzu GCMS-QP5050A; HP-5 column; 30 m-long×0.25 mm i.d.×0.25 μm thickness). Furfural conversion=35.1 wt % and furan selectivity=100 wt %. Finally, furan was separated from the liquid product by distillation.

Example 4

This example illustrates the conversion of furfural to furan and 2-methyl furan over Pt(5 wt %)/$Al_2O_3$ catalyst. 1 g of furfural, 20 g of de-ionized water were taken in a 100 ml stainless-steel reactor (Parr 4875 power controller and 4871 process controller). To that 0.05 g of the reduced Pt(5 wt %)/$Al_2O_3$ catalyst was added. The reactor was pressurized with nitrogen gas to a pressure of 5 bar. Temperature of the reactor was raised to 240° C. and the reaction was conducted for 2 h. Then the reactor was cooled to 25° C., gaseous product was vented out for further recycling purpose. Liquid product was separated from the catalyst by filtration and it was then subjected to analysis by gas chromatography (GC; Varian 3400; CP-SIL5CB column; 60 m-long and 0.25 mm-i.d.). The products were identified by GC-MS (Shimadzu GCMS-QP5050A; HP-5 column; 30 m-long×0.25 mm i.d.×0.25 μm thickness). Furfural conversion=29.2%, furan selectivity=43.1% and others including 2-methyl furan selectivity=56.8%. Furan and 2-methyl furan were separated from the liquid product by distillation.

Example 5

This example illustrates the conversion of furfural to furan over Pd(5 wt %)/$Al_2O_3$ catalyst in the presence of water-isopropanol (1:4) medium. 1 g of furfural, 20 g of isopropanol and 5 g of water were taken in a 100 ml stainless-steel reactor (Parr 4875 power controller and 4871 process controller). To that 0.05 g of the reduced Pd(5 wt %)/$Al_2O_3$ catalyst was added. The reactor was pressurized with nitrogen gas (5 bar). Temperature of the reactor was raised to 240° C. and the reaction was conducted for 2 h. Then the reactor was cooled to 25° C., gas was vented out for recycle purpose and the liquid product was separated from the catalyst by filtration. It was then subjected to analysis by gas chromatography (GC; Varian 3400; CP-SIL5CB column; 60 m-long and 0.25 mm-i.d.). The products were identified by GC-MS (Shimadzu GCMS-QP5050A; HP-5 column; 30 m-long×0.25 mm i.d.×0.25 μm thickness). Furfural conversion=99.7 wt % and furan selectivity=82.5 wt %. Finally, furan was separated from the liquid product by distillation.

Example 6

This example illustrates the conversion of furfural to furan and 2-methyl furan over Pd(5 wt %)/$Al_2O_3$ catalyst in the presence of water-isopropanol (1:1) medium. 1 g of furfural, 10 g of isopropanol and 10 g of water were taken in a 100 ml stainless-steel reactor (Parr 4875 power controller and 4871 process controller). To that 0.05 g of the reduced Pd(5 wt %)/$Al_2O_3$ catalyst was added. The reactor was pressurized with nitrogen gas (5 bar). Temperature of the reactor was raised to 240° C. and the reaction was conducted for 2 h. Then the reactor was cooled to 25° C., gas was vented out for recycle purpose and the liquid product was separated from the catalyst by filtration. It was then subjected to analysis by gas chromatography (GC; Varian 3400; CP-SIL5CB column; 60 m-long and 0.25 mm-i.d.). The products were identified by GC-MS (Shimadzu GCMS-QP5050A; HP-5 column; 30 m-long×0.25 mm i.d.×0.25 μm thickness). Furfural conversion=30.0 wt %, furan selectivity=83.3 wt % and others including 2-methyl furan selectivity=13.2 wt %. Finally, furan and 2-methyl furan were separated from the liquid product by distillation.

Example 7

This example illustrates the conversion of furfural to furan and 2-methyl furan over Pt(5 wt %)/$Al_2O_3$ catalyst. 1 g of furfural, 20 g of iso-propanol and 5 g of de-ionized water were taken in a 100 ml stainless-steel reactor (Parr 4875 power controller and 4871 process controller). To that 0.05 g of the reduced Pt(5 wt %)/$Al_2O_3$ catalyst was added. The reactor was pressurized with nitrogen gas to a pressure of 5 bar. Temperature of the reactor was raised to 240° C. and the reaction was conducted for 2 h. Then the reactor was cooled to 25° C., liquid product was separated from the catalyst by filtration and it was then subjected to analysis by gas chromatography (GC; Varian 3400; CP-SIL5CB column; 60 m-long and 0.25 mm-i.d.). The products were identified by GC-MS (Shimadzu GCMS-QP5050A; HP-5 column; 30 m-long×0.25 mm i.d.×0.25 μm thickness). Furfural conversion=93.5%, furan selectivity=76.5% and others including 2-methyl furan selectivity=23.5 wt %. Finally, furan and 2-methyl furan were separated from the liquid product by distillation.

Example 8

This example illustrates the conversion of furfural to furan and 2-methyl furan over Pt(5 wt %)/$Al_2O_3$ catalyst in the presence of hydrogen and water-isopropanol (1:4) solvent medium. 1 g of furfural, 20 g of iso-propanol and 5 g of de-ionized water were taken in a 100 ml stainless-steel reactor (Parr 4875 power controller and 4871 process controller). To that 0.05 g of the reduced Pt(5 wt %)/$Al_2O_3$ catalyst was added. The reactor was pressurized with hydrogen gas to a pressure of 20 bar. Temperature of the reactor was raised to 240° C. and the reaction was conducted for 2 h. Then the reactor was cooled to 25° C., liquid product was separated from the catalyst by filtration and it was then subjected to analysis by gas chromatography (GC; Varian 3400; CP-SIL5CB column; 60 m-long and 0.25 mm-i.d.). The products were identified by GC-MS (Shimadzu GCMS-QP5050A; HP-5 column; 30 m-long×0.25 mm i.d.×0.25 μm thickness). Furfural conversion=100 wt %, furan selectivity=53.0 wt % and 2-methyl furan selectivity=15.6 wt %. Finally, furan and 2-methyl furan were separated from the liquid product by distillation.

Example 9

This example illustrates the conversion of furfural to furan and 2-methyl furan over Pt(5 wt %)/$SO_4$—$ZrO_2$ catalyst in the presence of hydrogen and isopropanol medium. 1 g of furfural, 20 g of iso-propanol and 5 g of water were taken in a 100 ml stainless-steel reactor (Parr 4875 power controller and 4871 process controller). To that 0.05 g of the reduced Pt(5 wt %)/$Al_2O_3$ catalyst was added. The reactor was pressurized with hydrogen gas to a pressure of 20 bar. Temperature of the reactor was raised to 240° C. and the reaction was conducted for 8 h. Then the reactor was cooled to 25° C., liquid product was separated from the catalyst by filtration and it was then subjected to analysis by gas chromatography (GC; Varian 3400; CP-SIL5CB column; 60 m-long and 0.25 mm-i.d.). The products were identified by GC-MS (Shimadzu GCMS-QP5050A; HP-5 column; 30 m-long×0.25 mm i.d.×0.25 μm thickness). Furfural conversion=100 wt %, furan selectivity=33.3 wt % and 2-methyl furan selectivity=47.2 wt %. Finally, furan and 2-methyl furan were separated from the liquid product by distillation.

Example 10

This example illustrates the conversion of furfural to furan over Pd(5 wt %)/$Al_2O_3$ catalyst without out using any inert gas. 1 g of furfural, 20 g of iso-propanol and 5 g of de-ionized water were taken in a 100 ml stainless-steel reactor (Parr 4875 power controller and 4871 process controller). To that 0.05 g of the reduced Pd(5 wt %)/$Al_2O_3$ catalyst was added. Temperature of the reactor was raised to 225° C. and the reaction was conducted for 2 h. Then the reactor was cooled to 25° C., liquid product was separated from the catalyst by filtration and it was then subjected to analysis by gas chromatography (GC; Varian 3400; CP-SIL5CB column; 60 m-long and 0.25 mm-i.d.). The products were identified by GC-MS (Shimadzu GCMS-QP5050A; HP-5 column; 30 m-long×0.25 mm i.d.×0.25 μm thickness). Furfural conversion=92 wt %, furan selectivity=75 wt %.

Example 11

This example illustrates the conversion of furfural to furan derived from the pentosan sugars of lignocellulosic biomass over Pd(5 wt %)/$Al_2O_3$ catalyst in the presence of water-isopropanol (4:1) medium. 1 g of biomass-derived furfural, 20 g of isopropanol and 5 g of water were taken in a 100 ml stainless-steel reactor (Parr 4875 power controller and 4871 process controller). To that 0.05 g of the reduced Pd(5 wt %)/$Al_2O_3$ catalyst was added. The reactor was pressurized with nitrogen gas (5 bar). Temperature of the reactor was raised to 240° C. and the reaction was conducted for 2 h. Then the reactor was cooled to 25° C., gas was vented out for recycle purpose and the liquid product was separated from the catalyst by filtration. It was then subjected to analysis by gas chromatography (GC; Varian 3400; CP-SIL5CB column; 60 m-long and 0.25 mm-i.d.). The products were identified by GC-MS (Shimadzu GCMS-QP5050A; HP-5 column; 30 m-long×0.25 mm i.d.×0.25 μm thickness). Furfural conversion=99 wt % and furan selectivity=84 wt %. Finally, furan was separated from the liquid product by distillation.

Example 12

This example illustrates the conversion of furfural to furan in a fixed-bed reactor. 20 g of Pd(5 wt %)/$Al_2O_3$ extrudates (1/16 inch diameter) were placed in between inert alumina extrudates which work as pre and post heaters in a fixed-bed reactor. The reactor was maintained at 240° C. and pressurized with nitrogen to 5 bar at those conditions. Reactant mixture in the weight ratio of 1:20 containing furfural and isopropanol: water (4:1) were fed to the reactor at weight hourly space velocity of 0.8 h$^{-1}$. The liquid product after passing the effluent through condenser and gas-liquid separator was collected and subjected to analysis by gas chromatography (GC; Varian 3400; CP-SIL5CB column; 60 m-long and 0.25 mm-i.d.). The products were identified by GC-MS (Shimadzu GCMS-QP5050A; HP-5 column; 30 m-long×0.25 mm i.d.×0.25 μm thickness). Furfural conversion=98 wt % and furan selectivity=83 wt %.

Example 13

This example illustrates the reusability and catalyst stability in long term studies of Pd(5 wt %)/Al$_2$O$_3$ catalyst. 5 g of furfural, 100 g of iso-propanol and 25 g of de-ionized water were taken in a 300 ml stainless-steel Parr reactor. To that 0.25 g of the reduced Pd(5 wt %)/Al$_2$O$_3$ catalyst was added. The reactor was pressurized with nitrogen gas to a pressure of 5 bar. Temperature of the reactor was raised to 240° C. and the reaction was conducted for 2 h. Then the reactor was cooled to 25° C., gases were vented out for recycle, liquid product was separated from the catalyst by filtration and it was then subjected to analysis by gas chromatography (GC; Varian 3400; CP-SIL5CB column; 60 m-long and 0.25 mm-i.d.). The products were identified by GC-MS (Shimadzu GCMS-QP5050A; HP-5 column; 30 m-long×0.25 mm i.d.×0.25 μm thickness). The catalyst separated was dried in at 100-110° C. for half-an-hour and reused in a subsequent recycle experiment conducted in the same as described above in this example. Six such catalyst recycling experiments were done. Furfural conversion on all the recycling experiments=99.7%, furan selectivity=82.7% (0$^{th}$ recycle), 82% (1$^{st}$ recycle), 83 (2$^{nd}$ recycle), 85% (3 recycle), 88% (4$^{th}$ recycle), and 90% (5$^{th}$ and 6$^{th}$ recycle).

Advantages of the Invention

Advantages of instant invention are as following:
i. Hydrogen-free process for producing furan from furfural;
ii. Reusable catalyst process;
iii. Sustainable process producing furan and 2-methyl furan from renewable, biomass-derived feedstock;
iv. Eco-friendly process with zero waste stream generation;
v. Furfural conversion of 100 mol % and furan selectivity of 75-90 mol %

The invention claimed is:

1. An improved process for the preparation of a compound of formula I from furfural

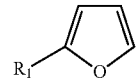

Formula I wherein R$_1$ is independently hydrogen or CH$_3$ comprising contacting furfural and water-isopropanol mixture with a supported metal catalyst in a reactor in the presence of a co-feed inert gas at a temperature in the range of 200-250° C., wherein the inert gas is at pressure in the range 1 to 10 bar so as to obtain the compound of formula I, and wherein the supported metal catalyst is a supported Pd or Pt catalyst.

2. The process as claimed in claim 1, wherein the ratio by weight of furfural to the water-isopropanol is in the 1:5 to 1:25.

3. The process as claimed in claim 1, wherein weight ratio of catalyst to furfural ranges between 2 and 5 wt %.

4. The process as claimed in claim 1, wherein the Pd or Pt catalyst content on the support ranges from 2-10 wt %.

5. The process as claimed in claim 4, wherein a support to the metal catalyst is selected from the group consisting of alumina, ceria, zirconia, ceria-zirconia, sulphated zirconia, silica, carbon, clay, hydrotalcite, MgO—Al$_2$O$_3$ and mixtures thereof.

6. The process as claimed in claim 1, wherein the reaction is carried out in a semi-batch, continuous stirred tank or a fixed-bed reactor.

7. The process as claimed in claim 1, wherein the inert gas is nitrogen gas, argon gas, helium gas or a mixtures of two or more of such gases.

8. The process as claimed in claim 1, wherein the water-iso-propanol ratio by weight in the mixture is between 1:1 and 1:5.

9. The process as claimed in claim 1, wherein the catalyst is a recyclable catalyst.

10. The process as claimed in claim 1, wherein the wt % furfural converted to the compound is in the range of 29-99.7 wt %.

11. The process as claimed in claim 1, wherein the yield of the compound of formula 1 is in the range of 68-90 wt %.

* * * * *